(12) United States Patent
Wilson et al.

(10) Patent No.: US 11,185,319 B2
(45) Date of Patent: Nov. 30, 2021

(54) SURGICAL DISTRACTOR AND METHOD

(71) Applicant: Warsaw Orthopedic, Inc., Warsaw, IN (US)

(72) Inventors: Madeline G. Wilson, Memphis, TN (US); Larry Thomas McBride, Memphis, TN (US); Jason M. May, Collierville, TN (US); Jeffrey Lynn Gum, Crestwood, KY (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 324 days.

(21) Appl. No.: 16/272,680

(22) Filed: Feb. 11, 2019

(65) Prior Publication Data

US 2020/0253593 A1    Aug. 13, 2020

(51) Int. Cl.
*A61B 17/02* (2006.01)
*A61B 17/66* (2006.01)
*A61B 17/70* (2006.01)
*A61B 17/00* (2006.01)

(52) U.S. Cl.
CPC ........ *A61B 17/025* (2013.01); *A61B 17/0206* (2013.01); *A61B 17/0218* (2013.01); *A61B 17/66* (2013.01); *A61B 17/7062* (2013.01); *A61B 17/7077* (2013.01); *A61B 2017/00358* (2013.01); *A61B 2017/0256* (2013.01)

(58) Field of Classification Search
CPC . A61B 17/0218; A61B 17/02; A61B 17/0206; A61B 17/025; A61B 17/7062; A61B 17/7077; A61B 17/8866; A61B 17/66; A61B 2017/00358; A61B 2017/00477; A61B 2017/0256; A61F 2/00

USPC ........... 606/90, 219, 201, 214, 224, 210, 53
See application file for complete search history.

(56) References Cited

U.S. PATENT DOCUMENTS

| | | | |
|---|---|---|---|
| 5,782,831 A * | 7/1998 | Sherman | A61B 17/7079 606/103 |
| 7,481,828 B2 | 1/2009 | Mazda et al. | |
| 7,585,299 B2 | 9/2009 | Rezach | |
| 7,618,424 B2 * | 11/2009 | Wilcox | A61B 17/025 606/105 |
| 7,959,654 B2 | 6/2011 | Mazda et al. | |
| 8,162,946 B2 | 4/2012 | Baccelli et al. | |
| 8,172,843 B2 | 5/2012 | Baccelli et al. | |
| 8,323,319 B2 | 12/2012 | Mazda et al. | |
| 8,465,527 B2 | 6/2013 | Clement | |
| 8,870,869 B2 | 10/2014 | Meunier et al. | |
| 8,870,881 B2 | 10/2014 | Rezach et al. | |
| 8,945,188 B2 | 2/2015 | Rezach et al. | |
| 9,173,685 B2 | 11/2015 | Lindquist et al. | |
| 9,241,739 B2 | 1/2016 | Mueller et al. | |
| 9,844,397 B2 | 12/2017 | Carls | |
| 9,872,713 B2 | 1/2018 | Simpson et al. | |
| 2003/0055319 A1 * | 3/2003 | Chang | A61B 17/0206 600/210 |

(Continued)

*Primary Examiner* — Marcela I. Shirsat
(74) *Attorney, Agent, or Firm* — Sorell, Lenna & Schmidt, LLP

(57) ABSTRACT

A surgical instrument comprises a first arm including a first closed loop engageable with a first spinal implant disposed with a first vertebral surface. A second arm is movable relative to the first arm and includes a second closed loop engageable with a second spinal implant disposed with a second vertebral surface. Surgical systems, constructs, implants and methods are disclosed.

20 Claims, 8 Drawing Sheets

(56) References Cited

U.S. PATENT DOCUMENTS

| | | |
|---|---|---|
| 2009/0248077 A1 | 10/2009 | Johns |
| 2011/0184469 A1 | 7/2011 | Ballard et al. |
| 2012/0296171 A1* | 11/2012 | Lovell .................. A61B 17/708 |
| | | 600/213 |
| 2014/0148854 A1 | 5/2014 | Carlson et al. |
| 2015/0282847 A1 | 10/2015 | Gordon et al. |
| 2015/0289906 A1 | 10/2015 | Murray et al. |
| 2016/0074029 A1* | 3/2016 | O'Connell ......... A61B 17/0218 |
| | | 600/213 |
| 2016/0106478 A1 | 4/2016 | Simpson et al. |

\* cited by examiner

SURGICAL DISTRACTOR AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In some embodiments, a surgical instrument is provided. The surgical instrument comprises a first arm including a first closed loop engageable with a first spinal implant disposed with a first vertebral surface. A second arm is movable relative to the first arm and includes a second closed loop engageable with a second spinal implant disposed with a second vertebral surface. In some embodiments, surgical systems, constructs, implants and methods are disclosed.

In some embodiments, the surgical instrument comprises at least one arm including at least one channel and a distal face. A cable has a first end, a second end and an arcuate portion. The ends are disposed with the at least one channel and the arcuate portion extends from the at least one arm in a closed loop with the distal face for disposal about a bone screw shank.

In some embodiments, a surgical system is provided. The surgical system comprises a distraction member. A first arm is connected with the distraction member and includes a closed loop engageable with a first spinal implant disposed with a first vertebral surface, A second arm is connected with the distraction member and is movable relative to the first arm. The second arm includes a closed loop engageable with a second spinal implant disposed with a second vertebral surface.

BRIEF DESCRIPTION OF THE DRAWINGS

The present disclosure will become more readily apparent from the specific description accompanied by the following drawings, in which.

DETAILED DESCRIPTION

Figure 1:
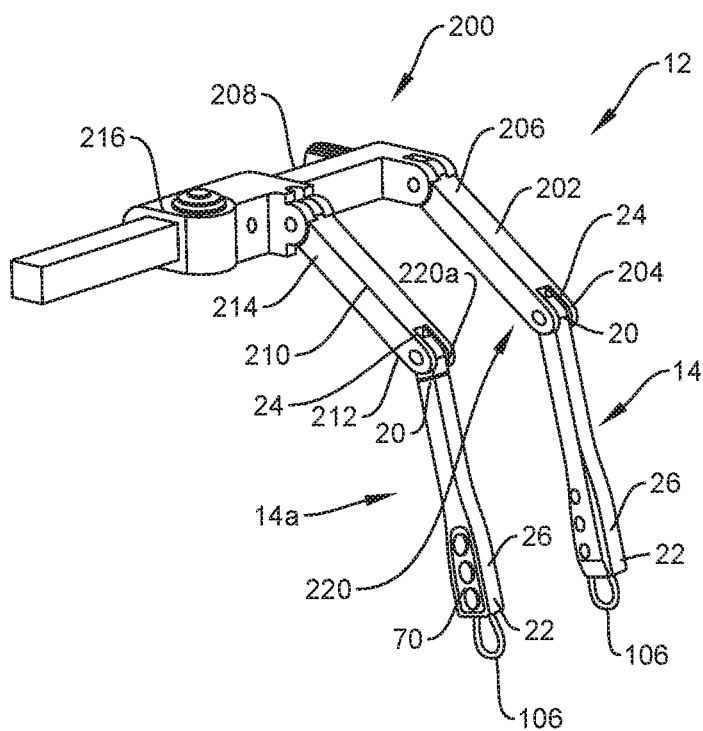
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system provides vertebral manipulation to treat spinal disorders, for example, managing lordosis and/or kyphosis restoration. In some embodiments, the present surgical system can be employed for a pedicle subtraction osteotomy (PSO). In some embodiments, the present surgical system can be employed with a posterior vertebral column resection to correct angular and fixed kyphotic deformity, such as post traumatic deformity, congenital deformity and/or post infectious deformity.

In some embodiments, the present surgical system comprises one or more surgical instruments, for example, a surgical distractor that allows for distraction and/or compression of vertebral tissue. In some embodiments, the present surgical system includes a surgical instrument, for example, a shank-based loop distractor. In some embodiments, the present surgical distractor includes a loop and/or lasso comprising a cable. In some embodiments, the present surgical distractor is configured to distract off bone screw shanks, while minimizing interference in a working surgical field and/or window. In some embodiments, the present surgical distractor is configured for a posterior midline surgical approach (MIDLF).

In some embodiments, the present surgical system comprises a surgical distractor including a housing unit having a stainless steel cable that forms a lasso at the distal end of the housing unit. In some embodiments, the lasso is clamped into the housing unit using a cap and set screws. In some embodiments, the lasso loops around a bone screw shank to distract vertebral tissue. In some embodiments, the surgical distractor includes one or more lasso and/or loops that can extend angularly, for example, from the distractor feet, in a selected angular orientation from a center plane or axis. In some embodiments, the lasso and/or loops can extend angularly at a zero degree orientation relative to the distractor feet or arms, for example, co-axially or co-incident. In some embodiments, the lasso and/or loops can extend angularly at a 22.5 degree orientation relative to the distractor feet or arms. In some embodiments, the surgical distractor includes a flexible cable that allows lassoing of a screw shank, which may include a screw shank disposed with difficult to access anatomy, varying bone screw configurations and/or varying screw trajectories. In some embodiments, the surgical distractor includes a cable fabricated from 17-4 stainless steel.

In some embodiments, the present surgical system comprises a surgical distractor employed with a method of assembly including the step of threading a single cable into openings of the surgical distractor to form a loop outside of the surgical distractor. In some embodiments, the cable includes ends that extend within two channels of the surgical distractor. In some embodiments, the surgical distractor includes a mating lid that clamps the cable within the channels. In some embodiments, the mating lid is screwed into place with the surgical distractor to achieve a selected clamp/pullout force. For example, the channels allow uniform placement of the cable with the surgical distractor. In some embodiments, the surgical distractor includes a distal end having a chamfer to maintain a low profile and minimize impingement on anatomy.

In some embodiments, the present surgical system is employed with a rack based distractor system. In some embodiments, the rack is connected with distractor feet, which are screwed into and semi-permanently attached with the rack to form a surgical distractor system. In some embodiments, the present surgical system is employed with pivoting grippers. In some embodiments, the surgical distractor includes arms having distal feet that are manipulated in a cephalad and/or caudal orientation. In some embodiments, the present surgical system is employed with a rack based distractor system and modular distractor arms so that a height of a loop can be selected and/or adjusted. In some embodiments, the surgical system can include modular distractor arms and/or feet that can be inserted into rack extensions or pivoting extensions or grippers, which are held in place with a ball detent. This configuration allows a height of the cable loop or lasso to be selected and/or adjusted.

In some embodiments, the present surgical system includes a surgical distractor employed with a method of treating a spine including the step of disposing a loop and/or lasso portion of at least one surgical distractor around a bone screw shank. In some embodiments, the method includes the step manipulating the bone screw shank to distract vertebral tissue. In some embodiments, the surgical distractor includes a flexible stainless steel cable loop or lasso that allows the distractor, which may include a rack or modular distractor, to loop around the shank. This configuration can be employed with difficult to access anatomy, varying bone screw configurations and/or varying screw trajectories. In some embodiments, the surgical distractor includes a loop or lasso having one or a plurality of degrees of freedom to maximize a surgical working window. In some embodiments, the surgical distractor includes a U-joint distractor engageable with a bone screw shank.

In some embodiments, the present surgical system is utilized with a transforaminal lumbar interbody fusion (TLIF) procedure. In some embodiments, a substantial portion of the shank extends in a cephalad caudal orientation. In some embodiments, a diameter of the shank is equal to or less than a diameter of a head of the bone screw. In some embodiments, the surgical distractor includes arms that are adjustable from a parallel orientation.

In some embodiments, the present surgical system includes a surgical distractor utilized with a method to correct complex spinal deformities. In some embodiments, the present surgical system includes a surgical distractor utilized with a method to treat degenerative spinal disorders and/or employed with transforaminal lumbar interbody fusion procedures. In some embodiments, the present surgical system includes a surgical distractor utilized with various configuration bone screws, for example, a sagittal adjusting screw (SAS), a fixed axis screw (FAS) and/or a multi-axial screw (MAS). In some embodiments, the present surgical system comprises a plurality of distractors, such as, for example, two distractors disposed along a side of vertebrae to perform a ligamentotaxy procedure. In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 includes a surgical instrument, such as, for example, a surgical distractor 12 having an arm 14 and an arm 14a disposed in a spaced apart relation to facilitate engagement with adjacent tissue for distraction of the tissue. In some embodiments, surgical instrument includes a retractor. Arms 14, 14a are connectable with a surgical instrument, such as for, example, a distraction member 200, as shown in FIG. 1, for manipulation of tissue, as described herein. Each of arms 14, 14a includes or is connected to a longitudinal element configured for engagement with a spinal implant, such as, for example, a shank 304 (see e.g., FIG. 9) of a bone screw 300 to facilitate manipulation of tissue, as described herein. Loop 106 is configured to lasso adjacent bone screws 300 to facilitate distraction. In some embodiments, distractor 12 is configured to minimize interference in a working surgical field and/or window. In some embodiments, distractor 12 may include one or a plurality of arms 14.

Figures 3, 4:
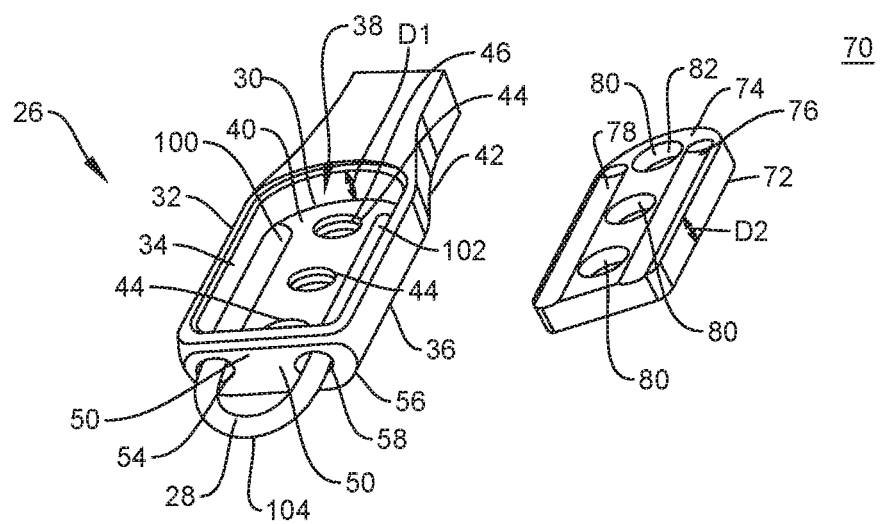
FIG. 3 is a cutaway view of components of the surgical system shown in FIG. 1.
FIG. 4 is a perspective view of components of the surgical system shown in FIG. 1.
Figure 5:
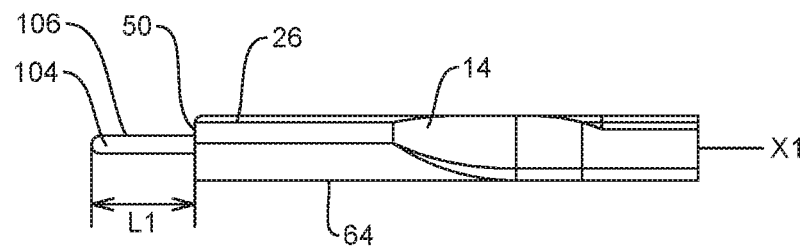
FIG. 5 is a side cutaway view of components of one embodiment of a surgical system in accordance with the principles of the present disclosure.

Each arm 14, 14a extends between a proximal end 20 and a distal end 22 along an axis X1, as shown in FIG. 5. End 20 includes a mating surface 24 configured for connection with distraction member 200, as described herein. End 22 includes a housing 26 and a longitudinal element, such as, for example, a cable 28 (FIG. 3). Cable 28 extends between an end 100, an end 102 and has an arcuate portion 104 disposed between ends 100, 102. Ends 100, 102 are disposed with housing 26 to form loop 106, as described herein.

In some embodiments, all or only a portion of the longitudinal element may have a semi-rigid, rigid, flexible or elastic configuration, and/or have elastic and/or flexible properties such as the elastic and/or flexible properties corresponding to the material examples described above such that the longitudinal element provides a selective amount of expansion and/or extension. The flexibility of the longitudinal element facilitates disposal of loop 106 around bone screw 300 that may be positioned with difficult and varying trajectories and/or impinging anatomy that may resist and/or prevent a rigid element to grasp and distract at an appropriate angle. The longitudinal element may include a plurality of separately attachable or connectable portions or sections (not shown in detail), such as bands or loops, or may be monolithically formed as a single continuous element.

In some embodiments, the longitudinal element includes a stainless-steel cable. In some embodiments, the longitudinal element may have various surface configurations, such as, for example, rough, threaded for connection with surgical instruments, arcuate, undulating, porous, semi-porous, dimpled, polished and/or textured. In some embodiments, a thickness defined by the longitudinal element may be uniformly increasing or decreasing or have alternative diameter dimensions along its length. In some embodiments, the longitudinal element may have any of various cross-sectional configurations, such as, for example, oval, oblong, triangular, rectangular, square, polygonal, irregular, uniform, non-uniform, variable and/or tapered.

In some embodiments, the longitudinal element may have various lengths. In some embodiments, the longitudinal element may be braided, such as a rope, or include a plurality of elongated elements to increase strength of the element, able to provide a higher predetermined resistance force.

Housing 26 includes a floor, including a surface 30, and a wall 32, as shown in FIG. 3. Wall 32 includes an inner surface 34 and an outer surface 36. Surface 34 of wall 32 and surface 30 define a cavity 38. Cavity 38 includes a depth D1. Wall 32 is disposed about all or a portion of cavity 38.

Surface 30 defines an elongated channel 40 disposed within cavity 38. Channel 40 extends parallel to axis X1. In some embodiments, channel 40 may be oriented in alternative configurations, such as, for example, co-axial, angularly offset, offset and/or staggered relative to axis X1. Channel 40 is configured for disposal of end 100 of cable 28, as described herein.

Surface 30 defines an elongated channel 42 disposed within cavity 38. Channel 42 is spaced apart from channel 40, as shown in FIG. 3. Channel 42 extends parallel to axis X1. In some embodiments, channel 42 may be oriented in alternative configurations, such as, for example, co-axial, angularly offset, offset and/or staggered relative to axis X1. Channel 42 is configured for disposal of end 102 of cable 28, as described herein.

Figure 6:
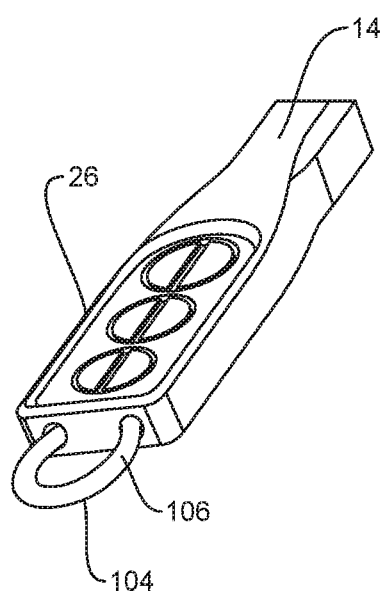
FIG. 6 is a break away view of components shown in FIG. 5.

Ends 100, 102 are disposed with channels 40, 42 such that arcuate portion 104 extends distally from housing 26 forming loop 106, as shown in FIGS. 5 and 6. Loop 106 extends a distance L1 relative to a distal face 50, as shown in FIG. 5. In some embodiments, distance L1 is adjustable via manipulation of ends 100, 102 within channels 40, 42 such that a size of loop 106 can be increased and/or decreased. The size of loop 106 can be measured in various ways, including by area within the loop, or general or effective radius or diameter of the loop, though the arcuate portion does not form a circle. In some embodiments, ends 100, 102 may be fixed with housing 26 in various configurations, such as, for example, disposed within cavity 38 and fixed with surface 30 by mating elements, such as, for example, clamp, clips, hooks, adhesives, spring loaded buttons, and/or flanges.

In some embodiments, arcuate portion 104 extends from arm 14 in alignment with axis X1, at a zero-degree orientation, relative to axis X1, as shown in FIGS. 5 and 6. In some embodiments, arcuate portion 104 may be oriented in alternative configurations, such as, for example, transverse, angular, offset and/or staggered relative to axis X1.

Figure 7:
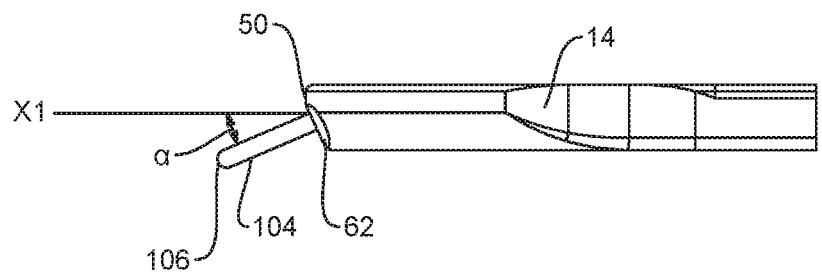
FIG. 7 is a side cutaway view of components of one embodiment of a surgical system in accordance with the principles of the present disclosure.
Figure 8:
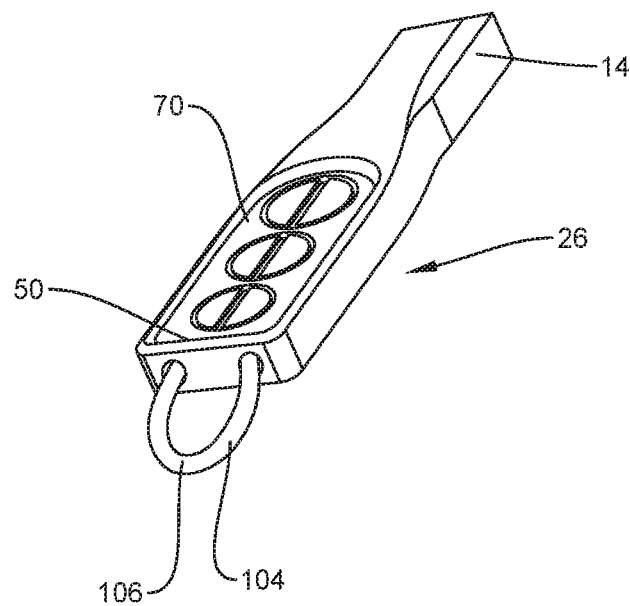
FIG. 8 is a break away view of components shown in FIG. 7.

In some embodiments, arcuate portion 104 extends from arm 14 in a transverse orientation relative to axis X1, as shown in FIGS. 7 and 8. In some embodiments, arcuate portion 104 extends at an angle α relative to axis X1. In some embodiments, angle α is in a range between about 0 degrees and about 90 degrees. In some embodiments, angle α is about 22.5 degrees to provide visualization of loop 106 when looking down from a surgeon's point of view. In some embodiments, angle α could be between about 22 degrees and about 23 degrees, between about 21 degrees and about 24 degrees, between about 20 degrees and about 25 degrees, etc., without departing from the scope of the present technology. In some embodiments, the orientation of arcuate portion 104 facilitates attachment of loop 106 with shank 304.

In some embodiments, arm 14 may include one or a plurality of channels, such as the channels 40, 42 mentioned above. In some embodiments, all or only a portion of channel 40 and/or channel 42 may have alternative surface configurations to enhance engagement with cable 28, such as, for example, rough, arcuate, undulating, mesh, porous, semi-porous, dimpled and/or textured. In one embodiment, housing 26 includes mating elements such as, for example, clips, hooks, adhesives, spring loaded buttons and/or flanges to connect with ends 100, 102.

Surface 30 includes one or more openings 44. Openings 44 include a thread form 46. Thread form 46 is configured for engagement with a coupling member, such as, for example, a setscrew 84, to fix ends 100, 102 with housing 26, as described herein. Engagement of setscrew 84 compresses ends 100, 102 to fix ends 100, 102 with housing 26, as described herein. In some embodiments, instead of by threads, surfaces of openings 44 are disposed with the coupling member in alternative fixation configurations, such as, for example, friction fit, pressure fit, locking protrusion/recess, locking keyway, and/or adhesive. In some embodiments, all or only a portion of the surface of openings 44 have alternative surface configurations to enhance engagement with setscrew 84, such as, for example, rough, arcuate, undulating, mesh, porous, semi-porous, dimpled, and/or textured.

Wall 32 includes distal face 50, as shown in FIG. 3. Distal face 50 defines an opening 54 extending through wall 32. Opening 54 is disposed in communication with channel 40 to facilitate insertion of end 100 into cavity 38 and disposal with channel 40. Opening 54 extends parallel to axis X1. In some embodiments, opening 54 may be oriented in alternative configurations, such as, for example, co-axial, angularly offset, offset and/or staggered relative to axis X1.

Distal face 50 defines an opening 58. Opening 58 is disposed in communication with channel 42 to facilitate insertion of end 102 into cavity 38 and disposal with channel 42. Opening 58 extends parallel to axis X1. In some embodiments, opening 58 may be oriented in alternative configurations, such as, for example, co-axial, angularly offset, offset and/or staggered relative to axis X1.

Figure 2:
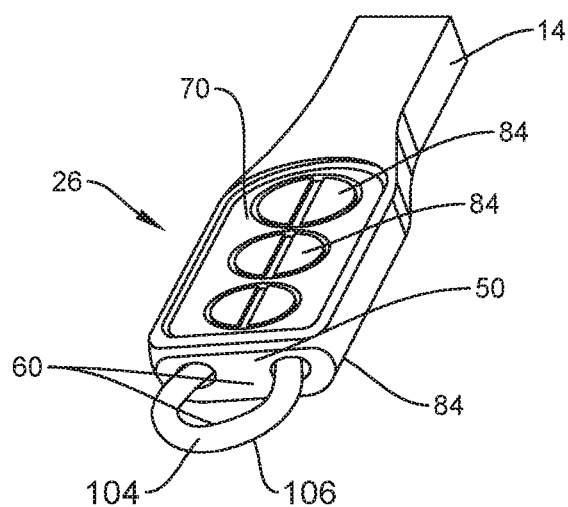
FIG. 2 is a break away view of components of the surgical system shown in FIG. 1.

Distal face 50 and loop 106 define a capture surface 60, as referenced in FIG. 2. Surface 60 is configured for disposal about an outer surface 308 of a shank 304, as described herein and shown in FIGS. 9 and 10. Loop 106 is configured to translate over a head 302 of bone screw 300 such that surface 60 is disposed about surface 308 of shank 304, as described herein.

In various embodiments, wall 32 includes an angled surface, such as, for example, a chamfered surface extending between a base 64 of housing 26 and distal face 50. The chamfered surface 22 is configured to maintain a low profile of surgical distractor 12 and minimize impingement on anatomy.

Housing 26 is attachable with a clamp 70, as shown in FIG. 3. Clamp 70 includes a body 72 shaped for a mating engagement with housing 26, as shown in FIGS. 2-4. Body 72 includes a depth D2. In some embodiments, depth D2 is equal to depth D1 such that a top surface of the body is generally flush with a top surface of wall 32.

In various embodiments, body 72 includes a surface 74 that defines an elongated channel 76. Channel 76 is configured for alignment with channel 40 for capture of end 100 therebetween. In various embodiments, surface 74 defines an elongated channel 78 spaced apart from channel 76, as shown in FIG. 4. Channel 78 is configured for alignment with channel 42 for capture of end 102 therebetween. In some embodiments, clamp 70 includes one or a plurality of channels. In some embodiments, all or only a portion of channel 76 and/or channel 78 has an alternate surface configuration to enhance engagement with cable 28, such as, for example, rough, arcuate, undulating, mesh, porous, semi-porous, dimpled, and/or textured. In some embodiments, surface 74 is configured to facilitate capture of ends 100, 102, such as by being, irregular, uniform, non-uniform, variable, and/or tapered.

Surface 74 includes one or more openings 80 in various embodiments. Openings 80 are configured for alignment with openings 44 upon disposal of clamp 70 with cavity 32. Setscrews 84 (FIG. 2) are disposed with openings 80, 44 such that engagement of the setscrews with the openings compresses ends 100, 102 to fix ends 100, 102 with housing 26. Each opening 80 can include a beveled surface 82 configured for disposal of a head of setscrew 84.

Figure 9:
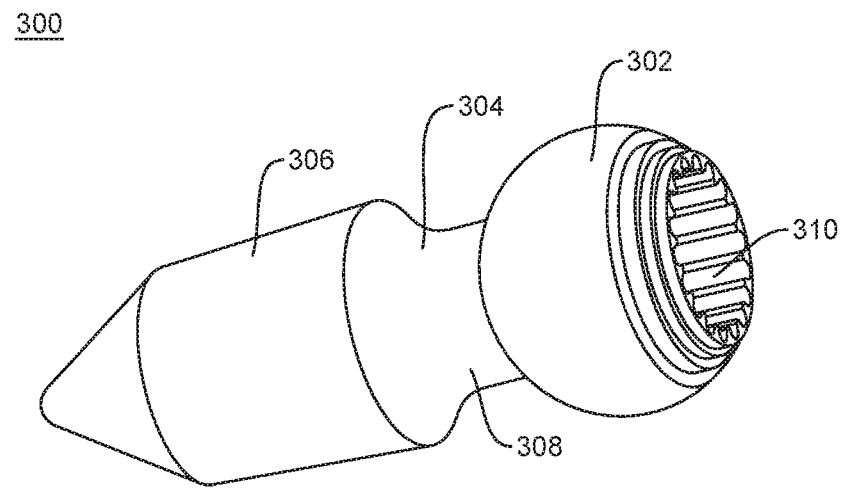
FIG. 9 is a perspective view of components of one embodiment of a system in accordance with the principles of the present disclosure.

Bone screw 300 includes a head 302, shank 304 and a shaft 306, as shown in FIG. 9. Shaft 306 is configured to penetrate tissue, such as, for example, vertebral tissue. In some embodiments, shaft 306 includes an outer surface having an external thread form (see e.g., FIG. 10). In some embodiments, the external thread form may include a single thread turn or a plurality of discrete threads, Shank 304 may be disposed between head 302 and shaft 306. Shank 304 includes outer surface 308, which in various embodiments has a circular configuration to facilitate engagement with capture surface 60, as described herein. In some embodiments, shank 304 may have alternative cross-sections, such as, for example, rectangular, polygonal, hexalobe, oval, hexagonal, or irregular. Head 302 includes a tool engaging portion 310 configured to engage a surgical tool or instrument, as described herein. In some embodiments, portion 308 includes a hexagonal cross-section. In some embodiments, portion 310 may have alternative cross sections, such as, for example, rectangular, polygonal, hexalobe, oval, or irregular.

Figure 10:
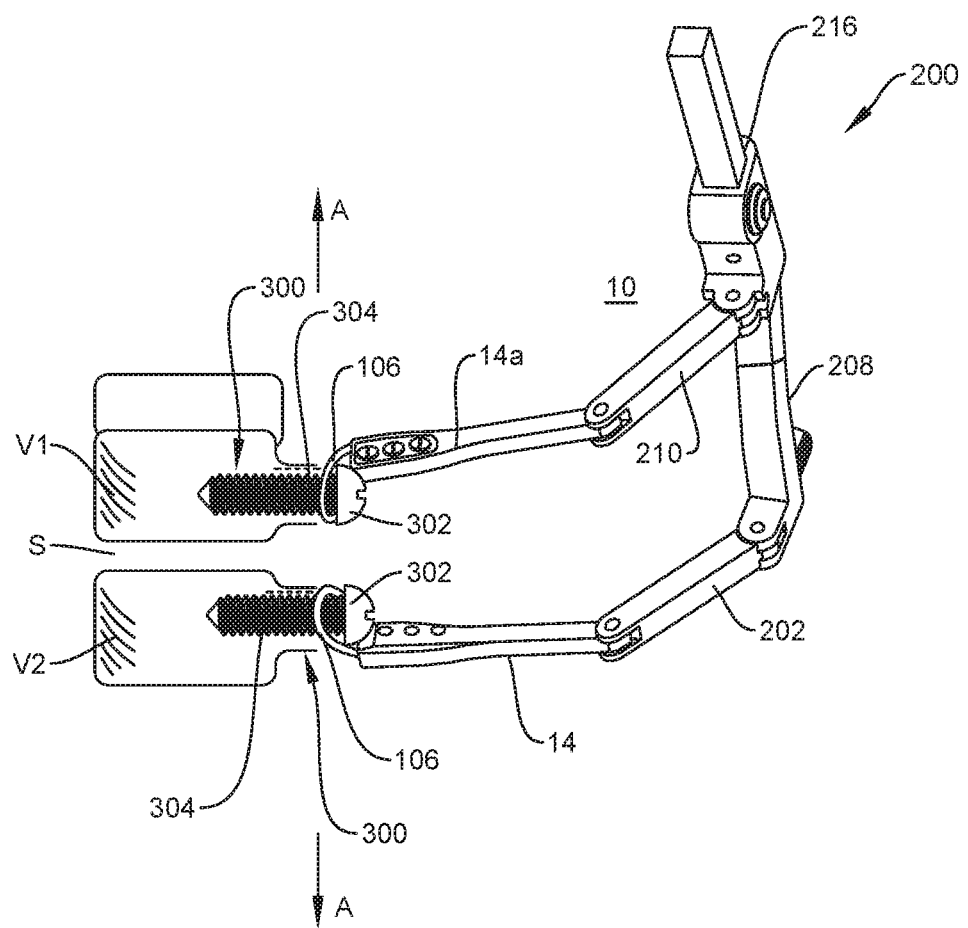
FIG. 10 is a side view of components of one embodiment of a system disposed with vertebrae in accordance with the principles of the present disclosure.

Arms 14, 14a are attached with distraction member 200 for relative translation to space apart tissue to which the arms are attached, as shown by way of example in FIG. 10. Member 200 includes an extension 202 configured for connection with arm 14. Extension 202 extends between an end 204 and an end 206. End 204 is attachable with arm 14 via a pivot mechanism 220 in various embodiments to facilitate manipulation of arm 14 relative to member 200, as described herein. The pivot mechanism 220 can be designed to allow pivoting of the arm 14 along a single plane with respect to the extension 202, or along any of multiple planes. In various embodiments, end 206 includes or is connected to a gear rack 208.

Extension 210 extends between an end 212 and an end 214. End 212 is attachable with arm 14a via a pivot mechanism 220a to facilitate manipulation of arm 14a relative to member 200, as described herein. The pivot mechanism 220a can be designed to allow pivoting of the arm 14a along a single plane with respect to the extension 210, or along any of multiple planes.

End 214 in various embodiments includes a gear 216 engageable with gear rack 208 to facilitate axial translation of extension 210 and arm 14a for distraction of tissue.

In a contemplated embodiment, the extensions 202, 210 are considered part of the arms 14, 14a, whether the extensions are movable, e.g., pivotable, with respect to the balance of the arm.

Pivot mechanisms 220, 220a are configured to allow arms 14, 14a to be movable in one or a plurality of degrees of freedom to one or a plurality of orientations relative to distraction member 200, stationary surgical equipment and/or the patient body in connection with a surgical procedure. In some embodiments, the degrees of freedom of movement of arms 14, 14a to one or a plurality of orientations relative to member 200, stationary surgical equipment and/or patient body can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality directions. In some embodiments, arms 14, 14a are independently and selectively movable relative to member 200, stationary surgical equipment and/or patient body. In some embodiments, one or a plurality of arms 14, 14a may be attachable with member 200.

In some embodiments, distractor 12 may be employed with various surgical instruments, such as, for example, drivers, extenders, reducers, spreaders, distracters, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, surgical system 10, similar to the systems and methods described herein, is employed with a surgical procedure, such as, for example, a treatment of an applicable condition or injury of an affected section of a spinal column and adjacent areas within a body. In some embodiments, one or all of the components of surgical system 10 can be delivered or utilized as a pre-assembled device or can be assembled in situ. Surgical system 10 may be completely or partially revised, removed or replaced.

In use, to treat vertebrae V, a medical practitioner obtains access to a surgical site in any appropriate manner, such as through incision and retraction of tissues. In some embodiments, spinal instrument system 10 can be used in any existing surgical method or technique including open surgery, mini-open surgery, minimally invasive surgery and percutaneous surgical implantation, whereby vertebrae V1, V2 are accessed through a mini-incision, or sleeve that provides a protected passageway to the area. Once access to the surgical site is obtained, the particular surgical procedure can be performed for treating the spine disorder, as shown in FIG. 10.

A drill (not shown) is utilized to create pilot holes in vertebra V1, V2. A driver (not shown) is connected with bone screws 300, as described herein. Bone screws 300 are engaged with tissue of vertebrae V1, V2. In some embodiments, bone screws 300 may be engaged with various portions of a vertebra, for example, anterior, posterior, interbody, intrabody, facet, laminae and/or one or more process.

In some embodiments, spinal instrument system 10 is employed with a pedicle subtraction osteotomy (PSO) procedure for treatment of an applicable condition or injury of an affected section of a spinal column and adjacent areas within a body. A preparation instrument (not shown) is employed to remove disc tissue, fluids, adjacent tissues and/or bone, and scrape and/or remove tissue from endplate surfaces of vertebra V1 and/or endplate surface of vertebra V2. In some embodiments, vertebral facets are resected. A discectomy is performed to create vertebral space S between vertebral bodies V1, V2.

Distractor 200 is oriented for connection with bone screws 300, as shown in FIG. 10. Arms 14, 14a are disposed adjacent bone screws 300. Loops 106 are translated and slide over in a contacting relation with head 302 for disposal about shank 304. Shank 304 is oriented with capture surface 60. The flexibility of cable 28 facilitates disposal of loop 106 around bone screws 300 that may be positioned with difficulty and varying trajectories and/or impinging anatomy that may resist and/or prevent a rigid element to grasp and distract at an appropriate angle. Distractor 200 is manipulated to translate one of arms 14 along rack 208 to facilitate distraction of vertebrae V.

During manipulation of distractor 200, capture surface 60 of each arm 14, 14a applies a force, in a direction shown by arrows A in FIG. 10, to surface 308 of shank 304. The force applied by capture surface 60 to bone screws 300 pulls and/or draws vertebrae V1, V2 apart to decompress intervertebral space S, relieve disc pressure, realign one or more vertebra and/or reduce compression on the spinal cord and adjacent nerves. In some embodiments, a spinal implant, such as, for example, an interbody implant (not shown) is disposed within intervertebral space S. The degrees of freedom associated with arms 14 and/or distractor 200 allow for the user to maximize a working window through which instruments will be passed and angulated during use.

In some embodiments, surgical system 10 may include one or a plurality of spinal constructs. In some embodiments, the spinal constructs may be disposed in various alternative orientations, such as, for example, side by side, parallel, transverse and/or other angular orientations such as acute or obtuse, co-axial and/or may be offset or staggered. In some embodiments, the spinal constructs including spinal rods may provide a template configuration for permanently implantable spinal rods, such as, implantable, final, permanent, removable, non-removable, bio-absorbable, resorbable and/or bio-degradable, and/or comprise permanently implantable spinal rods.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

Figure 11:
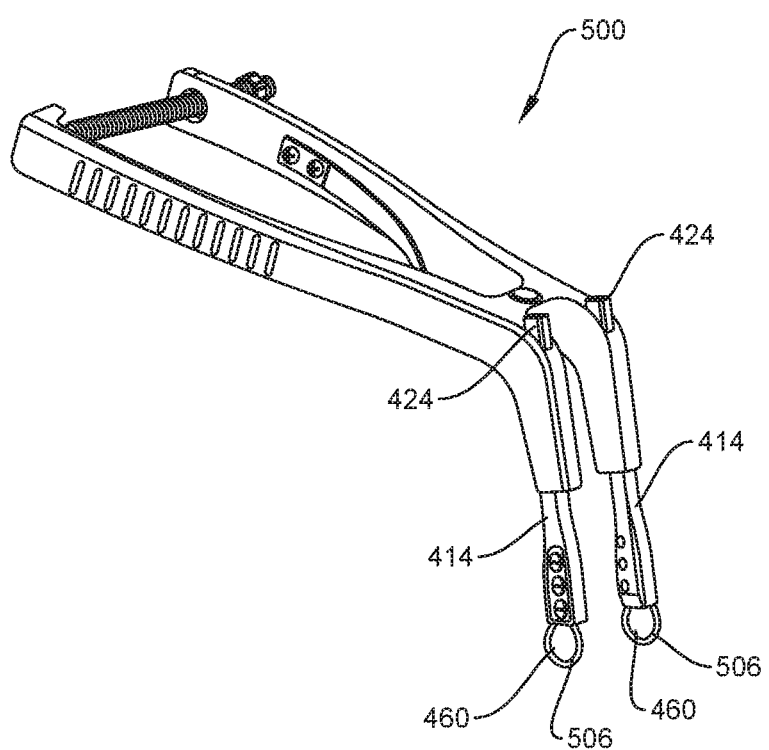
FIG. 11 is a perspective view of components of one embodiment of a system in accordance with the principles of the present disclosure.
Figure 12:
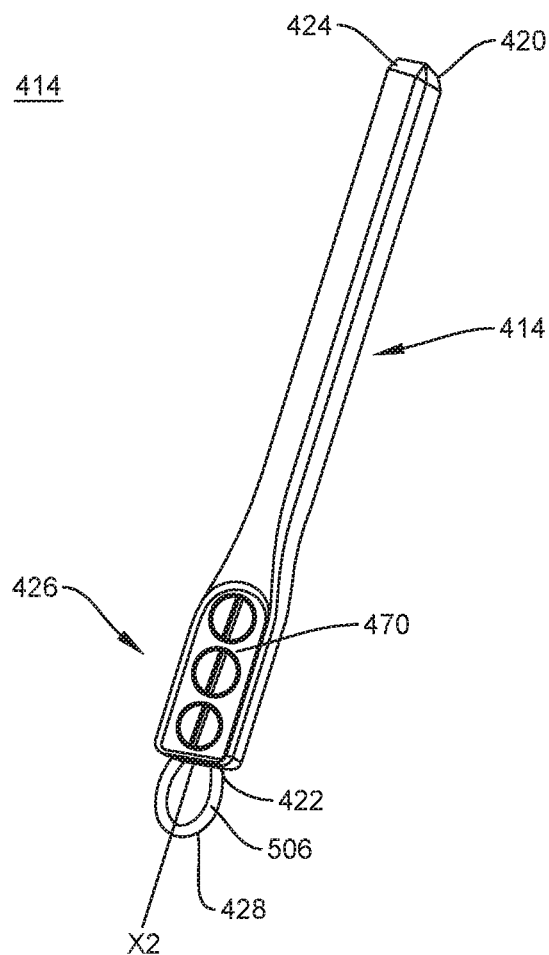
FIG. 12 is a perspective view of components of one embodiment of a system in accordance with the principles of the present disclosure.

In one embodiment, as shown in FIGS. 11 and 12, surgical system 10, similar to the systems and methods described herein, includes a surgical instrument, such as, for example, a surgical distractor or retractor 412 having a pair of arms, such as, for example, arms 414, similar to arms 14, 14a described herein. Arms 414 are connectable with a surgical instrument, such as for, example, a distraction member 500, as shown in FIG. 11. Arms 414 are interchangeable with distraction member 500 to comprise a surgical instrument having a selected orientation relative to distraction member 500. Each arm 414 includes a closed loop 506, similar to loop 106 described herein, configured for engagement with shank 304 of bone screw 300 to facilitate distraction of vertebrae, as described herein.

Each arm 414 extends between a proximal end 420 and a distal end 422 along an axis X2, as shown in FIG. 12. Each arm 414 is selected from a plurality of alternative arms 414. In some embodiments, surgical system 10 comprises a spinal implant kit, as described herein, which includes a plurality of arms 414 connectable with distraction member 500.

In some embodiments, loop 506 extends from arm 414 in alignment with axis X2, at a zero-degree orientation, relative to axis X2. In some embodiments, loop 506 may be oriented in alternative configurations, such as, for example, transverse, angular, offset and/or staggered relative to axis X2. In some embodiments, loop 506 extends from arm 414 in a transverse orientation relative to axis X2, as described herein. In some embodiments, loop 506 extends at an angle relative to axis X2, as described herein. In some embodiments, the orientation of loop 506 facilitates attachment of loop 506 with shank 304.

Each arm 414 can include a mating surface 424 disposed at end 420. The end 420 including the mating surface 424, and distraction member 500 are configured such that the mating surface 424 can be selectively and readily engaged to and disengaged from distraction member 500. In this way, each arm 414 is interchangeable with distraction member 500 for a selected orientation relative to distraction member 500, such as, for example, arm 414 can be positioned at various angles relative to distraction member 500 and/or may extend various distances from distraction member 500. In various embodiments, distraction member 500 and arm 414 includes a ball detent to facilitate selective assembly and disassembly of arm 414 to/from distraction member 500.

End 422 includes a housing 426 and a cable 428, similar to housing 26 and cable 28 described herein. Cable 428 is connectable with housing 426, as described herein. Housing 426 is attachable with a clamp 470, similar to clamp 70 described herein, to fix cable 428 with housing 426. Distractor 500 causes a capture surface 460 of each arm 414 to apply a force to surface 308 of shank 304, as described herein. The force applied by capture surface 460 to bone screws 300 pulls and/or draws vertebrae apart to decompress intervertebral space S, relieve disc pressure, realign one or more vertebra and/or reduce compression on the spinal cord and adjacent nerves.

The system 10 described here in connection with FIGS. 11 and 12 can in any other way be like the system 10 as shown in connection with FIGS. 1-20.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first arm including a housing having a cavity and a threaded opening, the first arm comprising a cable having opposite first and second ends and an arcuate portion between the ends, the ends being positioned in the cavity, the arcuate portion being positioned outside of the cavity to define a first loop engageable with a first spinal implant configured to be disposed with a first vertebral surface, the first arm comprising a setscrew positioned in the threaded opening such that the setscrew compresses the ends to fix the ends to the housing; and
a second arm movable relative to the first arm via a distraction member and including a second loop engageable with a second spinal configured to be implant disposed with a second vertebral surface.

2. A surgical instrument as recited in claim 1, wherein a distal end of the first arm and the first loop define a capture surface configured to be disposed about an outer surface of the first spinal implant.

3. A surgical instrument as recited in claim 1, wherein at least one of the loops comprises a flexible cable.

4. A surgical instrument as recited in claim 1, wherein at least one of the loops comprises stainless steel cable.

5. A surgical instrument as recited in claim 1, wherein the first arm defines a longitudinal axis and the first loop extends distally from the first arm along the axis.

6. A surgical instrument as recited in claim 1, wherein the first arm defines a longitudinal axis and the first loop extends distally at an angle of 22.5 degrees relative to the axis.

7. A surgical instrument as recited in claim 1, wherein the first arm defines a longitudinal axis and the first loop extends distally at an angle in a range of 0 through about 90 degrees relative to the axis.

8. A surgical instrument as recited in claim 1, wherein the first spinal implant includes a bone screw shank.

9. A surgical instrument as recited in claim 1, wherein the first arm comprises a clamp, the clamp being removably coupled to the housing such that top surfaces of the ends directly engage the clamp and opposite bottom surfaces of the ends directly engage the housing.

10. A surgical instrument as recited in claim 9, wherein the clamp comprises a bore, the setscrew extending through the bore.

11. A surgical instrument as recited in claim 10, wherein the clamp includes first and second channels extending into a surface of the clamp, the housing including third and fourth channels extending into a surface of the housing, the first end being positioned in the first and third channels, the second end being positioned in the second and fourth channels.

12. A surgical instrument as recited in claim 1, wherein:
the threaded opening includes a first threaded opening, a second threaded opening and a third threaded opening; the setscrew includes a first setscrew, a second setscrew and a third set screw; and
the first setscrew is disposed in the first threaded opening, the second setscrew is disposed in the second threaded opening and the third setscrew is disposed in the third threaded opening.

13. A surgical instrument comprising:
at least one arm including a housing, the housing comprising a threaded opening, at least one channel and a distal face;
a cable having a first end, a second end and an arcuate portion, the ends being disposed within the at least one channel and the arcuate portion extending from the at least one arm in a loop with the distal face for disposal about a bone screw shank; and
a setscrew positioned in the threaded opening such that the setscrew compresses the ends to fix the ends to the housing.

14. A surgical distractor as recited in claim 13, wherein the at least one arm includes a first arm and a second arm movable relative to the first arm in a configuration to distract vertebral tissue.

15. A surgical system comprising:
a distraction member;
a first arm connected with the distraction member and including a housing having a cavity and a threaded opening, the first arm comprising a cable having opposite first and second ends and an arcuate portion between the ends, the ends being positioned in the cavity, the arcuate portion being positioned outside of the cavity to define a loop engageable with a first spinal implant configured to be disposed with a first vertebral surface, the first arm comprising a setscrew positioned in the threaded opening such that the setscrew compresses the ends to fix the ends to the housing; and
a second arm connected with the distraction member and being movable relative to the first arm, the second arm including a loop engageable with a second spinal implant configured to be disposed with a second vertebral surface.

16. A surgical system as recited in claim 15, wherein a portion of the distraction member includes a gear rack engageable with a portion of the distraction member having a gear surface such that the first arm is axially translatable relative to the second arm.

17. A surgical system as recited in claim 15, wherein the distraction member includes extensions connected with the arms, the extensions being connected via a pivot such that the arms are relatively movable.

18. A surgical system as recited in claim 15, wherein at least one of the arms is movable about a plurality of axes relative to the distraction member.

19. A surgical system as recited in claim 15, wherein the arms are selected from a kit having a plurality of alternative sized arms for a selected orientation, each arm including a mating surface engageable with the distraction member such that the arm is interchangeable with the distraction member to comprise a surgical instrument having the selected orientation relative to the distraction member.

20. A surgical system as recited in claim 15, wherein the distraction member includes a portion of a ball detent connection arrangement for connecting to the arms.

* * * * *